(12) United States Patent
Robinson

(10) Patent No.: US 6,544,177 B1
(45) Date of Patent: Apr. 8, 2003

(54) ULTRASONIC DIAGNOSTIC IMAGING SYSTEM AND METHOD WITH HARMONIC SPATIAL COMPOUNDING

(75) Inventor: Andrew L. Robinson, Bellevue, WA (US)

(73) Assignee: ATL Ultrasound, Inc., Bothell, WA (US)

( * ) Notice: Subject to any disclaimer, the term of this patent is extended or adjusted under 35 U.S.C. 154(b) by 0 days.

(21) Appl. No.: 09/657,767

(22) Filed: Sep. 8, 2000

Related U.S. Application Data

(63) Continuation-in-part of application No. 09/335,058, filed on Jun. 17, 1999, now Pat. No. 6,210,328.
(60) Provisional application No. 60/102,923, filed on Oct. 1, 1998.

(51) Int. Cl.[7] ................................................. A61B 8/00
(52) U.S. Cl. ..................................................... 600/443
(58) Field of Search ................................. 600/443, 437, 600/447, 444, 448, 449; 73/625, 626

(56) References Cited

U.S. PATENT DOCUMENTS

| | | | |
|---|---|---|---|
| 4,159,462 A | 6/1979 | Rocha et al. | 367/97 |
| 4,319,489 A | 3/1982 | Yamaguchi et al. | 73/626 |
| 4,649,927 A | 3/1987 | Fehr et al. | 600/443 |
| 4,751,846 A | 6/1988 | Dousse | 73/602 |
| 5,255,683 A | 10/1993 | Monaghan | 600/458 |
| 5,410,516 A | 4/1995 | Uhlendorf et al. | 367/7 |
| 5,485,842 A | 1/1996 | Quistgaard | |
| 5,538,004 A | 7/1996 | Bamber | 600/443 |
| 5,566,674 A | 10/1996 | Weng | 600/443 |
| 5,575,286 A | 11/1996 | Weng et al. | 600/444 |
| 5,608,690 A | 3/1997 | Hossack et al. | 367/138 |
| 5,655,535 A | 8/1997 | Friemel et al. | 600/443 |
| 5,706,819 A | 1/1998 | Hwang et al. | |
| 5,782,766 A | 7/1998 | Weng et al. | 600/443 |
| 5,833,613 A | 11/1998 | Averkiou et al. | 600/440 |
| 5,860,924 A | 1/1999 | Quistgaard | |
| 5,879,303 A | 3/1999 | Averkiou et al. | 600/447 |
| 5,908,390 A | 6/1999 | Matsushima | 600/447 |
| 5,951,478 A | 9/1999 | Hwang et al. | 600/433 |
| 5,957,852 A * | 9/1999 | Hossack et al. | 600/458 |
| 6,014,897 A | 1/2000 | Mo | 73/628 |
| 6,074,347 A * | 6/2000 | Resnick et al. | 600/443 |
| 6,102,865 A | 8/2000 | Hossack et al. | |
| 6,117,081 A * | 9/2000 | Jago et al. | 600/443 |
| 6,126,598 A * | 10/2000 | Entrekin et al. | 600/437 |

OTHER PUBLICATIONS

Feigenbaum, Harvey, Echocardiography, Lea & Febiger, pp. 32–34, 1976, Philadelphia, PA.
Carpenter et al., Technical Note—A Multimode Real Time Scanner, Ultrasound in Med. & Biol., vol. 6, pp. 279–284, Pergamon Press Ltd., 1980, Great Britain.
Berson et al., Compound Scanning with a Electrically Steered Beam, Ultrasonic Imaging 3, pp. 303–308, Academic Press, Inc., 1981.
Shattuck et al., Compound Scanning with a Phased Array, Ultrasonic Imaging 4, pp. 93–107, Academic Press, Inc., 1982.
Jesperson et al., Multi–Angle Compound Imaging, Ultrasonic Imaging 20, pp. 81–102, Dynamedia, Inc., 1998.

* cited by examiner

Primary Examiner—Francis J. Jaworski
Assistant Examiner—Maulin Patel
(74) Attorney, Agent, or Firm—Dorsey-Whitney, LLP

(57) ABSTRACT

An ultrasonic diagnostic imaging system and method uses harmonic imaging to acquire a plurality of images at a variety of look angles. The number of acquired ultrasonic images that are compounded to form a spatially compounded image is varied in response to changes in system operating parameters initiated directly or indirectly by the system user.

84 Claims, 5 Drawing Sheets

ULTRASONIC DIAGNOSTIC IMAGING SYSTEM AND METHOD WITH HARMONIC SPATIAL COMPOUNDING

CROSS-REFERENCE TO RELATED APPLICATIONS

This application is a continuation-in-part of U.S. patent application Ser. No. 09/335,058, filed Jun. 17, 1999, now U.S. Pat. No. 6,210,328 which claims the benefit of U.S. Provisional Patent Application Ser. No. 60/102,923, filed Oct. 1, 1998.

TECHNICAL FIELD

The invention relates to ultrasonic diagnostic imaging systems and methods and, in particular, to ultrasonic diagnostic imaging systems that produce spatially compounded images and harmonic ultrasonic imaging systems.

BACKGROUND OF THE INVENTION

Spatial compounding is an imaging technique in which a number of ultrasonic images of a given target that have been obtained from multiple vantage points or angles (look directions) are combined into a single compounded image by combining the data received from each point in the compound image target which has been received from each angle. Examples of spatial compounding are described in U.S. Pat. Nos. 4,649,927; 4,319,489; and 4,159,462. Real time spatially compound imaging is performed by rapidly acquiring a series of partially overlapping component image frames from substantially independent spatial directions, and utilizing an array transducer to implement electronic beam steering and/or electronic translation of the component frames. The component frames are combined into a compounded image by summation, averaging, peak detection, or other combinational means. The acquisition sequence and formation of compounded images are repeated continuously at a rate limited by the acquisition frame rate, that is, the time required to acquire the full complement of scanlines over the selected width and depth of imaging.

The compounded image typically shows lower speckle and better specular reflector delineation than conventional ultrasonic images from a single viewpoint. Speckle is reduced (i.e., speckle signal to noise ratio is improved) by the square root of N in a compound image with N component frames, provided that the component frames used to create the compounded image are substantially independent and are averaged. Several criteria can be used to determine the degree of independence of the component frames (see, e.g., O'Donnell et al. in IEEE Trans. UFFC v.35, no.4, pp 470–76 (1988). In practice, for spatially compound imaging with a steered linear array, this implies a minimum steering angle between component frames that is typically on the order of several degrees.

The second way that spatially compound scanning improves image quality is by improving the acquisition of specular interfaces. For example, a curved bone-soft tissue interface produces a strong echo when the ultrasonic beam is exactly perpendicular to the interface, and a very weak echo when the beam is only a few degrees off perpendicular. These interfaces are often curved, and with conventional scanning only a small portion of the interface is visible. Spatially compound scanning acquires views of the interface from many different angles, making the curved interface visible and continuous over a larger field of view. Greater angular diversity generally improves the continuity of specular targets. However, the angular diversity available is limited by the acceptance angle of the transducer array elements. The acceptance angle depends on the transducer array element pitch, frequency, and construction methods.

Another ultrasonic imaging modality is harmonic ultrasonic imaging. It has been known for some time that tissue and fluids have inherent nonlinear properties. Tissue and fluids will, even in the absence of a contrast agent, develop and return their own non-linear echo response signals, including signals at harmonics of the fundamental. Muir and Carstensen explored these properties of water beginning in 1980, and Starritt et al. looked at these properties in human calf muscle and excised bovine liver.

While these non-linear echo components of tissue and fluids are generally not as great in amplitude as the harmonic components returned by harmonic contrast agents, they do exhibit a number of characteristics that have been recognized as being advantageous in conventional ultrasonic imaging. In particular, it has been recognized that negligible harmonic signals are generated very close to the transducer, which allows for clutter reduction when imaging through narrow orifices such as the ribs since fundamental signal reverberations are not being used for imaging. Additionally, it has been recognized that the levels of a harmonic beam side lobe are lower than the corresponding levels of the side lobes of the fundamental beam, which has implications for off-axis clutter reduction. Finally, it has been recognized that the main lobe of the harmonic is narrower than that of its fundamental, which allows for improved lateral resolution.

Although each of these modalities—spatially compounded imaging and harmonic imaging—has advantages in certain situations, each has certain performance limitations. In particular, the performance of ultrasonic imaging systems using spatial compounding is limited because grating lobes generated by a transducer array may cause false returns to be generated. With reference to FIG. 1 which shows a narrow-band example, an ultrasonic array 10 transmits and receives an ultrasonic signal having a main lobe 14 and a plurality of pairs of grating lobes, only one of which 18 is shown in FIG. 1. The grating lobes 18 are shown with an amplitude that is significantly less than the amplitude of the main lobe 14 because of the limited angular response of the transducer elements. The main lobe 14 has a higher amplitude because the main lobe 14 is transmitted by the array 10 with a higher sensitivity, and the main lobe 14 is received by the array 10 with a higher sensitivity. As is well known in the art, the grating lobe equation is: $\sin \phi_M - \sin \phi_G = \lambda/P$, where $\phi_M$ is the angle of the main lobe and $\phi_G$ is the angle of the grating lobe, both relative to the Y-axis. For a look angle of 0 degrees ($\phi_M$ equals 0 degrees), the angle $\theta$ between the main lobe 14 and the grating lobes 18 is given by the formula: $\theta = \sin^{-1} \lambda/P$, where P is the pitch of the array 10, i.e., the center-to-center distance between elements of the array 10, and $\lambda 0$ is the wavelength of the ultrasonic signal. When the wavelength $\lambda$ of the transmitted ultrasonic signal is equal to the pitch P of the array 10, the angle $\theta$ between the main lobe 14 and the grating lobes 18 is 90 degrees. As a result, an ultrasonic signal is not transmitted into tissues T positioned adjacent the array 10 through the grating lobes 18 so that the only image generated is an image resulting from insonification by the main lobe 14. Therefore, the grating lobes 18 do not present any problem when the main lobe 18 is directed straight into the tissues T and the angle $\theta$ between the main lobe 14 and the grating lobes 18 is 90 degrees or more, as shown in FIG. 1. If, however, the angle $\theta$ between the main lobe 14 and the grating lobes 18 is 45 degrees, as shown in FIG. 2, ultrasonic signals are transmitted through the grating lobes 18 into the tissues, and echoes are returned from the tissues T through the grating lobes 18. As a result, the image generated is an image resulting from the main lobe 14 as well as clutter and possibly a "false image" resulting from the grating lobes 18.

In spatial compounding, the tissue must be imaged from a variety of beam steering angles or look directions, as shown in FIG. 3. A spatially compounded image of an object O in the tissues T is the result of returns from the array 10 at a first angle $\phi_1$, returns from the array 10 at a second angle $\phi_2$, returns from the array 10 at a third angle $\phi_3$, etc. For the array 10 to image at each of these angles $\phi_3$, it is necessary for the array 10 to steer the main lobe 14 to such angle $\phi_1$, for example, as shown in FIG. 4. When the main lobe 14 is steered to an angle $\phi_1$, the grating lobes 18 are positioned at an angle so that one of the grating lobes 18a extends into the tissues T at an angle at which the array has greater sensitivity. Under these circumstances, ultrasonic returns are received from both the main lobe 14, and the grating lobe 18, and these returns are indistinguishable and thus both contribute to the ultrasonic image. The returns from the grating lobe 18 therefore result in clutter or a false image because they do not emanate from the object O being imaged. The result is an image of the object O cluttered by returns from tissues imaged by the grating lobe 18. This clutter can make it very difficult to view the object O being imaged. This problem might be alleviated to some extent by reducing the pitch P of the array 10 and/or increasing the wavelength of the transmitted ultrasonic, but there are limitations on the practical ability to either increase pitch P or decrease the wavelength beyond certain limits.

The problem of grating lobe clutter is even more acute as the angle $\phi$ of the main lobe 14 is increased, which is highly desirable for beam steering during spatially compound imaging. As shown in FIG. 5, the sensitivity A (both transmit and receive) of the array 10 is a function of the angle $\phi$ of a lobe, whether the lobe is a main lobe 14 or a grating lobe 18. When the main lobe 14 has an angle $\phi_{M1}$ equal to 0 degrees, as shown in FIG. 1, the sensitivity A of the main lobe 14 is relatively large, as shown in FIG. 5. At the same time, the sensitivity A of the grating lobe 18 is relatively small because the angle $\phi_{G1}$ of the grating lobe 18 is -90 degrees, as also shown in FIG. 5. However, when the main lobe 14 is steered to a relatively large angle $\phi_{M2}$ of 80 degrees, one of the grating lobes 18 is at an angle $\phi_{G2}$ of -1 degree. As a result, the amplitude of the fundamental lobe 14 is relatively small and the amplitude of the grating lobe 18 is relatively large, as also shown in FIG. 5. The problem of grating lobe clutter is therefore more severe with spatially compound imaging where beams are steered over a wide range of steering angles.

There is therefore a need for a system and method for spatially compound imaging that does not suffer from image clutter resulting from grating lobe returns.

SUMMARY OF THE INVENTION

A harmonic ultrasonic compounded imaging system and method uses a transducer array to transmit ultrasonic signals at a fundamental frequency. The transmitted ultrasonic signals have a main lobe that is directed at a target in a plurality of look directions. The transducer array then receives ultrasonic echo signals at a harmonic frequency by suitable means, such as by using a receive beamformer coupled to the transducer array and a filter or pulse inversion processor. The ultrasonic signals at the harmonic frequency have main lobes that are aligned in each of the look directions as the fundamental frequency main lobes. A spatially compounded image is then generated from the received ultrasonic signals at the harmonic frequency using, for example, a compound image processor. The ultrasonic signals at the fundamental frequency may have a grating lobe in addition to the main lobe. The ultrasonic signals in the grating lobe are transmitted in a direction that is different from the direction the ultrasonic signals in the main lobe are transmitted. Similarly, the received ultrasonic signals at the harmonic frequency may have a grating lobe in addition to the main lobe. The direction of the grating lobe of the received harmonic signals is different from the direction of the grating lobe of the transmitted fundamental signals so that the amplitude of any ultrasonic signals received through the grating lobe at the harmonic frequency is relatively low. In addition for steering angles at which the main lobe still has appreciably higher amplitude than the grating lobe, the non-linear nature of harmonic generation results in an increase in the relative amplitudes of the main and grating lobes at the harmonic frequency.

DETAILED DESCRIPTION OF THE INVENTION

Figure 1:
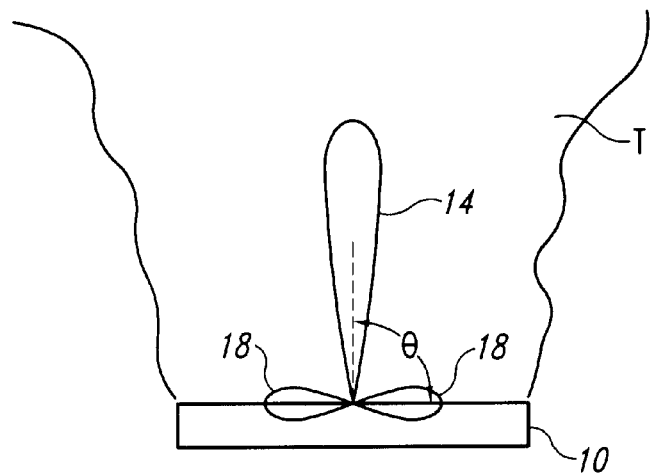
FIG. 1 is a schematic diagram illustrating the manner in which a fundamental ultrasonic signal having a first frequency is conventionally transmitted by a transducer array.
Figure 2:
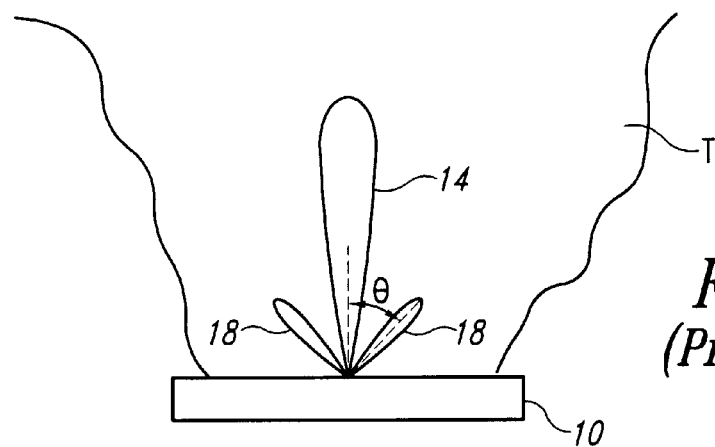
FIG. 2 is a schematic diagram illustrating the manner in which a fundamental ultrasonic signal having a second frequency is conventionally transmitted by a transducer array.
Figure 3:
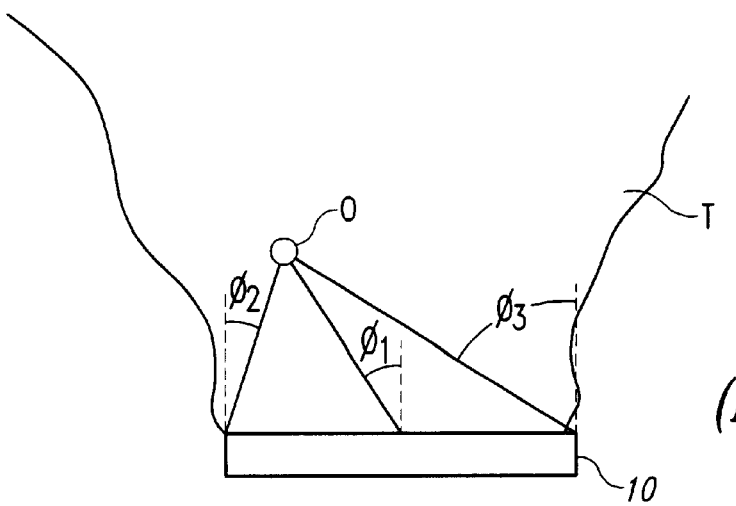
FIG. 3 is a schematic diagram illustrating the manner in which a transducer array conventionally images a target at multiple look angles to provide a spatially compounded ultrasonic image.
Figure 4:
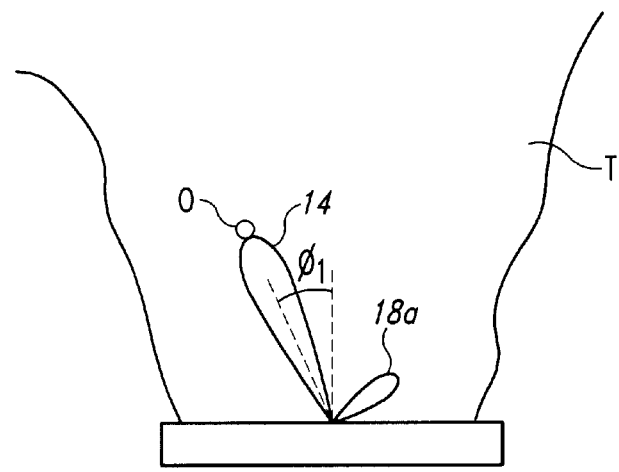
FIG. 4 is a schematic diagram illustrating the manner in which a transducer array conventionally images a target at one look angle during spatially compound imaging.
Figure 5:
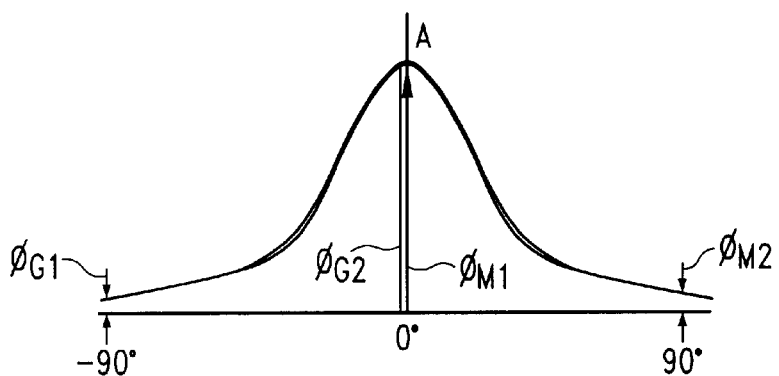
FIG. 5 is a graph showing the gain and sensitivity of a conventional transducer array as a function of look angle.
Figure 6:
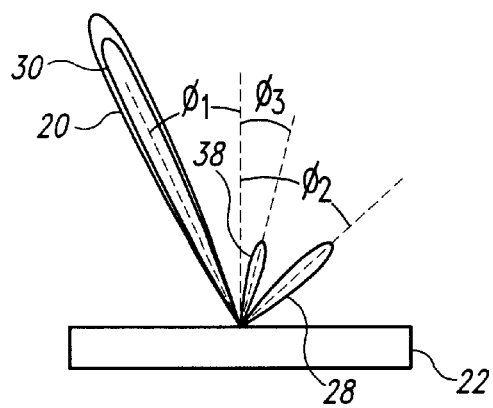
FIG. 6 is a schematic diagram illustrating the manner in which a transducer array images a target at one look angle during spatially compound imaging in accordance with an embodiment of the invention.

The manner in which the problem of grating lobe clutter in spatial compounding can be reduced in accordance with one embodiment of the invention is illustrated in FIG. 6. FIG. 6 shows a main lobe 20 transmitted at a fundamental frequency by an ultrasonic array 22 at a "look angle" of $\phi_1$. Also shown is a grating lobe 28 transmitted at the fundamental frequency at an angle of $\phi_2$. The array 22 receives ultrasonic signals at higher and sub harmonics of the fundamental frequency, in this example drawn for the second harmonic. A main lobe 30 of the harmonic signals has the same look angle $\phi_1$ as the main lobe 20 of the fundamental signals so that the array 22 will receive harmonic signals from the same direction in which the fundamental signals were transmitted. However, since the frequency of the harmonic signals is twice the frequency of the fundamental signals, the wavelength λ of the harmonic signals is half the wavelength λ of the fundamental signals. The ratio λ/P, and a resulting look angle $\phi_3$, of a harmonic grating lobe 38 is therefore different from the ratio λ/P, and the resulting look angle $\phi_2$, of the fundamental grating lobe 28. The array 22 thus receives ultrasonic signals through the harmonic grating lobe 38 in a direction that is different from the direction that ultrasonic signals are transmitted through the fundamental grating lobe 28. Since there are no ultrasonic signals transmitted in the direction from which the ultrasonic signals are received through the harmonic grating lobe 38, the harmonic grating lobe 38 does not cause appreciable clutter of an image generated using the harmonic main lobe 30. The use of harmonic imaging for spatially compound imaging thus produces results that are not possible when using the fundamental to generate an image through spatial compounding.

In practice, when a broadband transmit signal is used, both main and grating lobes are spread out as a function of the frequencies (and wavelengths) of the transmit signal. Under these circumstances there is opportunity for overlap between the fundamental and harmonic grating lobes. However, for steering angles at which the fundamental main lobe is greater than the fundamental grating lobe, an additional mechanism helps reduce the amplitude of the harmonic grating lobe. That mechanism is that the generation of harmonic signal is by nature non-linear, meaning that, for a case where the fundamental main lobe has twice the amplitude of its grating lobe, there will be more than a factor of two between the harmonic signals generated by the fundamental main and grating lobes.

Harmonic spatially compound imaging has the additional advantage of using a lower fundamental transmit frequency (e.g., ⅔ $f_0$) for an array of a given pitch, thus increasing the angle between the main lobe 20 of the fundamental and the grating lobe 28 of the fundamental. This means that the grating lobe at the fundamental frequency is even lower than it would be for operation at a frequency $f_0$ in the conventional case.

Figure 7:
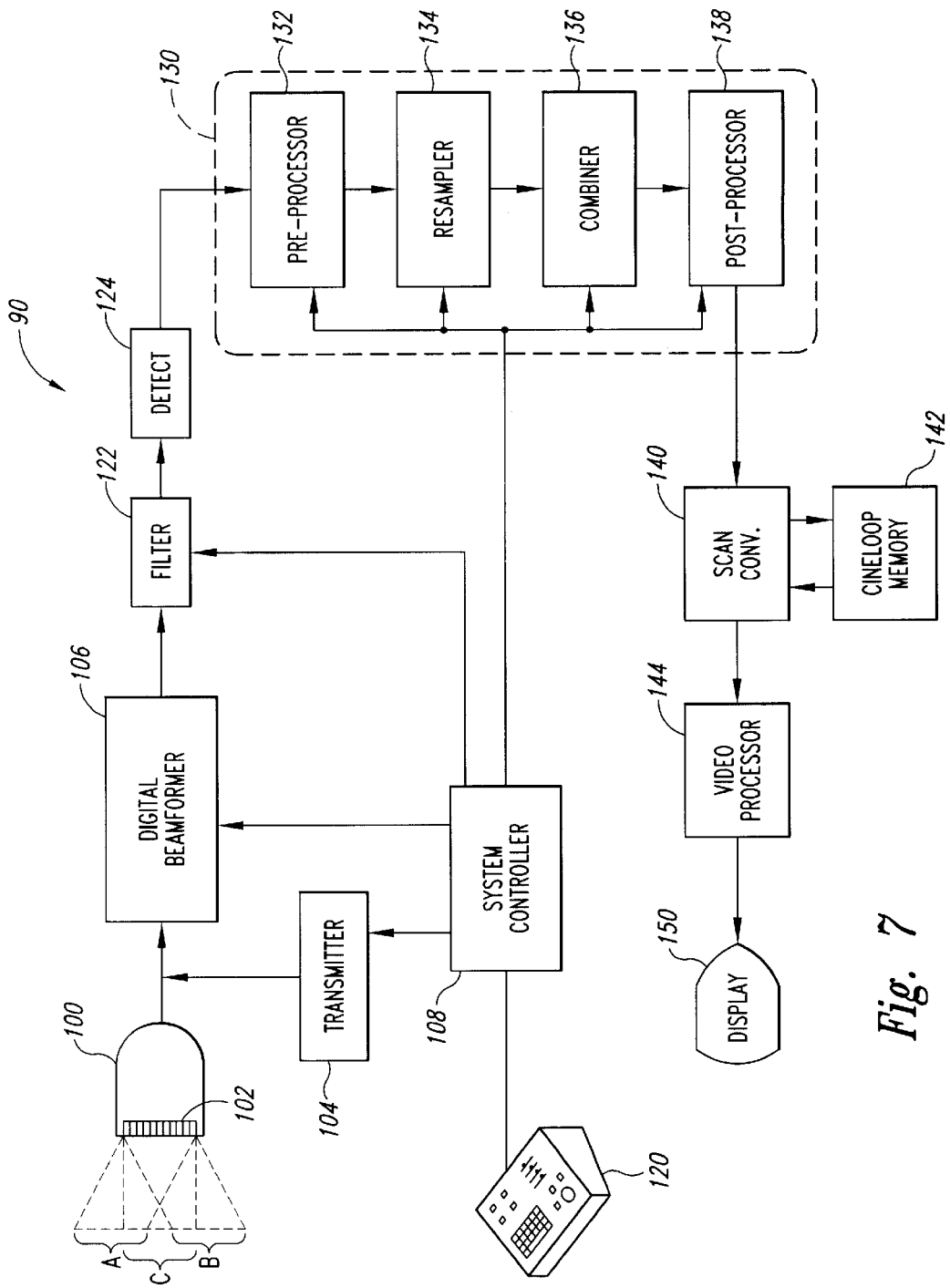
FIG. 7 is a block diagram of a system for generating a spatially compounded harmonic ultrasonic image in accordance with one embodiment of the invention.

One embodiment of a system 90 and method in accordance with the invention is shown in FIG. 7. The system 90 includes a scanhead 100 having a transducer array 102 that transmits beams at different angles over an image field denoted by the dashed rectangle and parallelograms. Three groups of scanlines are indicated in the drawing, labeled A, B, and C, with each group being steered at a different angle relative to the scanhead 100. The transmission of the beams is controlled by a transmitter 104, which controls the phasing and time of actuation of each of the elements of the array 102 so as to transmit each beam from a predetermined origin along the array and at a predetermined angle. The echoes returned from along each scanline are received by the elements of the array 102, digitized as by analog to digital conversion, and coupled to a digital beamformer 106. The digital beamformer 116 delays and sums the echoes from elements of the array 102 to form a sequence of focused, coherent digital echo samples along each scanline. The transmitter 104 and beamformer 106 are operated under control of a system controller 108, which in turn is responsive to the settings of controls on a user interface 120 operated by the user of the ultrasonic system. The system controller 108 controls the transmitter 104 to transmit the desired number of scanline groups at the desired angles, transmit energies and frequencies. The system controller 108 also controls the digital beamformer 106 to properly delay and combine the received echo signals for the apertures and image depths used.

The scanline echo signals are filtered by a programmable digital filter 122, which defines the band of frequencies of interest. The passband of the filter 122 is set to pass harmonics of the signal that is transmitted by the transmitter 104. As an alternative to separating the harmonic signals by filtering, pulse inversion processing may be employed as described in U.S. Pat. Nos. 5,706,819 (for harmonic contrast agents) and U.S. Pat. No 5,951,478 (for tissue harmonic signals), by which echoes received from a target in response to multiple, differently modulated transmit pulses are combined to cancel linear signals while emphasizing non-linear (e.g., second harmonic) signals. The transmitted signal may be a single fundamental frequency, two or more fundamental frequencies, or a band of frequencies centered at a nominal fundamental frequency. In any case, the signal passed by the filter 122 will be a single harmonic frequency, two or more harmonic frequencies, or a band of frequencies centered at a nominal harmonic frequency, respectively. The filtered harmonic signals are then detected by a detector 124. The filter 122 and detector 124 preferably include multiple filters and detectors so that the received signals may be separated into multiple passbands, individually detected and recombined to reduce image speckle by frequency compounding. For B mode imaging, the detector 124 will perform amplitude detection of the echo signal envelope. For Doppler imaging, ensembles of echoes are assembled for each point in the image and are Doppler processed to estimate the Doppler shift or Doppler power intensity.

The digital echo signals are processed by spatial compounding in a processor 130. A pre-processor 132 can preweight the signal samples if desired with a weighting factor. The samples can be preweighted with a weighting factor that is a function of the number of component frames used to form a particular compound image. The pre-processor 132 can also weight edge lines that are at the edge of one overlapping image so as to smooth the transitions where the number of samples or images which are compounded changes. The pre-processed signal samples may then undergo a resampling in a resampler 134. The resampler 134 can spatially realign the estimates of one component frame to those of another component frame or to the pixels of the display space.

After resampling, the image frames are compounded by a combiner 136. Combining may comprise summation, averaging, peak detection, or other combinational means. The samples being combined may also be weighted prior to combining in this step of the process. Finally, post-processing is performed by a post-processor 138. The post-processor 138 normalizes the combined values to a display range of values. Post-processing can be most easily implemented by look-up tables and can simultaneously perform compression and mapping of the range of compounded values to a range of values suitable for display of the compounded image.

The compounding process may be performed in estimate data space or in display pixel space. In one embodiment, scan conversion is done following the compounding process by a scan converter 140. The compound images may be stored in a Cineloop memory 142 in either estimate or display pixel form. If stored in estimate form, the images may be scan converted when replayed from the Cineloop memory 142 for display. The scan converter 140 and Cineloop memory 142 may also be used to render three dimensional presentations of the spatially compounded images as described in U.S. Pat. Nos. 5,485,842 and 5,860,924, or displays of an extended field of view by overlaying successively acquired, partially overlapping images in the lateral dimension. Following scan conversion, the spatially compounded images are processed for display by a video processor 144 and displayed on an image display 150.

Figure 8:
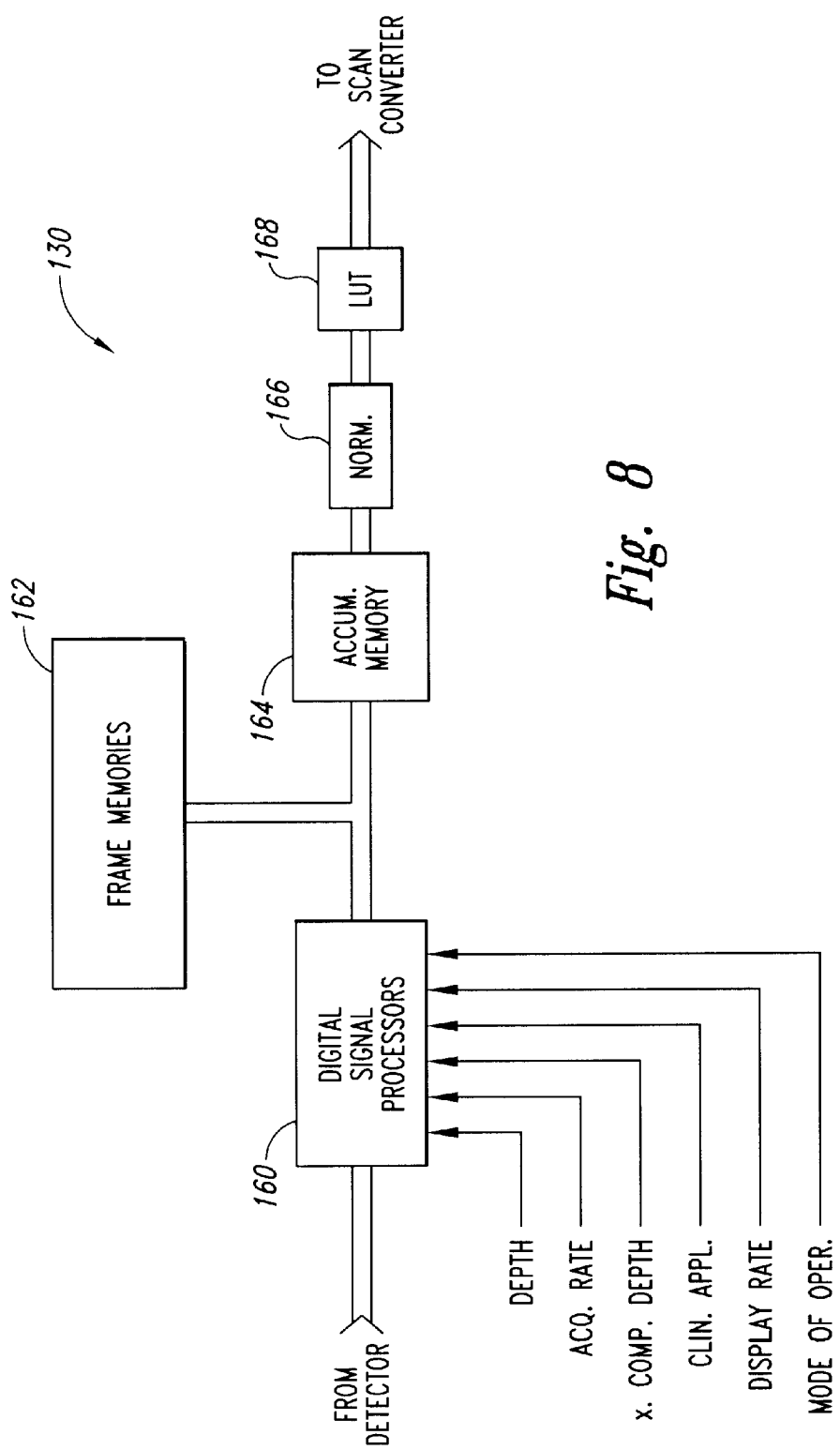
FIG. 8 is a block diagram of one embodiment of a processor used in the system of FIG. 7.

FIG. 8 illustrates one embodiment of the spatial compounding processor 130 of FIG. 7. The processor 130 is preferably implemented by one or more digital signal processors 160, which process the image data in various ways. The digital signal processors 160 can weight the received image data and can resample the image data to spatially align pixels from frame to frame, for instance. The digital signal processors 160 direct the processed image frames to a plurality of frame memories 162, which buffer the individual image frames. The number of image frames capable of being stored by the frame memories 162 is preferably at least equal to the maximum number of image frames to be compounded, such as sixteen frames. The digital signal processors 160 are responsive to changes in system control parameters including image display depth, number of scanlines or line density, number of transmit focal zones, amount of deadtime per pulse repetition interval (PRI), number of transmissions per image line, depth of region of greatest compounding, clinical application, number of simultaneous modes, size of region of interest, mode of operation, and acquisition rate for determining the number of component frames to compound at a given point in time. The digital signal processors select component frames stored in the frame memories 162 for assembly as a compound image in accumulator memory 164. The compounded image formed in the accumulator memory 164 is weighted or mapped by a normalization circuit 166, then compressed to the desired number of display bits and, if desired, remapped by a lookup table (LUT) 168. The fully processed compounded image is then transmitted to the scan converter 140 for formatting and display.

The digital signal processors 160 determine the number of frames that are to be compounded to improve image quality while still providing an acceptable realtime compound image frame rate. Increasing the number of component frames does not lead to a proportional or unlimited increase in the image quality of the compound image. There is, therefore, a practical maximum number of frames, each steered by a minimum angle, that can be usefully employed to improve image quality in spatially compound scanning. This number can vary widely depending on the transducer design and size of the active aperture, but can be as large as 16 component frames per compound image for an array with a large acceptance angle and small active apertures. The maximum useful number of frames will also depend on the mixture of speckle and anisotropic scatterers in the tissue of interest, and therefore on the clinical application.

The system 90 has particular utility when the clinician is changing between "survey" and "target" modes of operation. During the survey mode of operation, the clinician is rapidly maneuvering the scanhead 100 to quickly ascertain the presence of prominent physiological landmarks or features. The compounding of a large number of component frames when the scanhead 100 is in motion will result in blurred images. Consequently the number component frames being compounded is reduced during the survey mode. As the clinical operator identifies potential abnormalities, the scanhead motion is slowed down or stopped completely to image the features of interest ("targeted" or "study" mode). At this point, the image features within the component frames are more highly correlated, and motion blurring in the compound image is substantially reduced or completely eliminated as long as the scanhead 100 is substantially stationary. During the target mode, the number of component frames being compounded is increased to produce high quality images without the consequence of blurring.

It is well known that the frame rate of an image with a given line density is dependent upon the maximum display depth of the image, because the speed of sound in tissue (~1.54 millimeters per microsecond) imposes a minimum round trip propagation delay of 13 microseconds for every centimeter of image depth. Typically, additional delay time is also added to prevent reverberation artifacts, i.e., the receipt of echoes at the beginning of one image line which are returning from deep depths of a previous image line. For an image consisting of 192 ray lines and a depth of 2 centimeters, the acquisition frame rate can be 100 frames per second or greater, but for an 8 centimeter image depth the frame rate can drop to 25 frames per second. While 25 frames per second is adequate for real time examination, a compound image frame rate for 7 component frames at this depth is less than 4 frames per second. A frame rate this slow would generally be considered inadequate for real time examination. Conversely, a compound image with 3 component frames with an image depth of 2 centimeters would have a compound frame rate of 33 frames per second, which is higher than necessary for real time examinations.

Figure 9A:
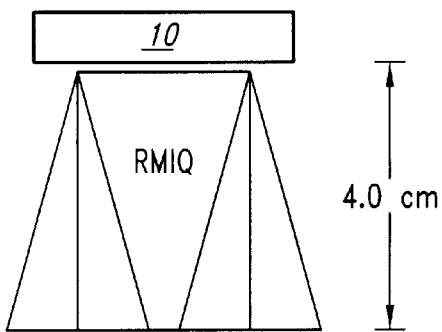
FIGS. 9a–c are diagrams schematically illustrating the effects of increasing and decreasing the number of acquired frames that are compounded to form a spatially compounded harmonic ultrasonic image using the system of FIG. 7.
Figure 9B:
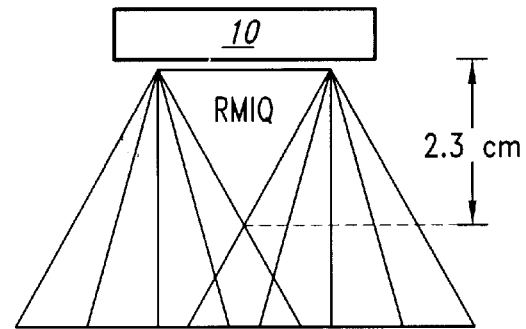
Figure 9C:
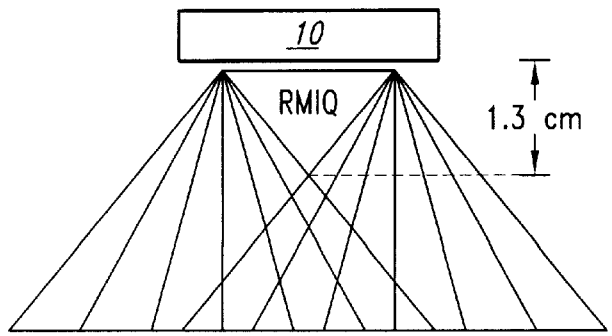

Compound harmonic scanning with a steered linear array results in a pattern of overlapping component frames such that the region of maximum image quality (RMIQ) where all N frames overlap is a trapezoidal or an inverted triangular region with its base at the top of the compound image. For a small number of component frames steered at the minimum angle, this region of maximum image quality extends deep into the compound image. For a large number of component frames, the RMIQ is relatively shallow. This is illustrated by FIGS. 9a–9c, which show three different compound scan geometries, each consisting of several partially overlapping steered linear component frames scanned from a linear array scanhead 100. For visual clarity, the minimum steering angle was chosen as 15° between component frames. FIG. 9a shows two component frames, which are compounded, and the RMIQ extends he full 4.0 cm height of the image. FIG. 9b shows an image that compounds four component frames, and the RMIQ now extends only 2.3 cm from the top of the compound frame. Similarly, FIG. 9c shows that, for seven component frames, the RMIQ of the compound image only extends 1.3 centimeters in depth. These drawings show that increasing the number of frames in the compound image decreases the size of the RMIQ. Thus, spatial compounding using component frames with large steering angles contributes very little additional image quality at depths deeper than the RMIQ.

It is apparent from the foregoing illustrations that that at shallow depths the frame rate is relatively high, which allows the use of more component frames (larger value of N) for spatially compound imaging while still maintaining an adequate frame rate of display. This is also consistent with the decrease in the depth of the RMIQ associated with more component frames (larger value of N) for spatially compound imaging. Therefore, the relationships between image depth, frame rate, the number of component frames in a spatially compounded image, the size and depth of the RMIQ, and image quality can be exploited to optimize overall performance. Table 1 below shows how these tradeoffs can advantageously be made for different depths, while always maintaining a compound frame rate of 10 Hz or greater.

TABLE 1

| Image display depth, cm | # of frames in compound image | Acquisition frame rate, Hz | Compound display rate, Hz | Max. steering angle, degrees | Depth of RMIQ, cm |
|---|---|---|---|---|---|
| 2 | 7 | 100 | 14 | 45 | 1.3 |
| 4 | 5 | 50 | 10 | 30 | 2.3 |
| 6 | 3 | 37.5 | 12.5 | 15 | 4.0 |
| 8 | 2 | 25 | 12.5 | 9 | 8.0 |

Thus it is seen that as the image display depth increases, the system controller 108 responds by decreasing the number of frames that are acquired and compounded to form the displayed compounded image. When the user selects a greater display depth for the scanhead 100, the ultrasonic system 90 responds by decreasing the number of frames of the compounded image. As the acquisition frame rate declines the number of frames compounded is also decreased. If the user reduces the frame rate, for example, by increasing the number of lines of an image, the ultrasonic system 90 will respond by decreasing the number of compounded frames in a displayed image. When the look directions of the acquired image frames are varied by steering the transmit beams in a number of different look directions, the angle of the sides of the trapezoidal-shaped image decreases with increases in the number of images that are compounded. These adaptive changes in the number of frames being compounded maintain the display rate of the compounded image at more than ten frames per second, or some other rate which is acceptable for the particular clinical application being performed.

As the number of frames compounded in the displayed image decreases, the depth of the region of greatest compounding preferably increases, but is comprised of fewer compounded image frames. As the image depth is decreased, the maximum steering angle of the steered transmit beams also preferably increases. A comparison of FIGS. 9a–9c illustrates how a greater maximum steering angle will more effectively cover a shallow imaging depth, whereas a lesser maximum steering angle is more effective for greater imaging depths.

Thus it is seen that the use of harmonic spatially compound imaging allows high quality of compounded images to be produced at a wide variety of look angles. The system 90 preferably operates by decreasing the number of look directions and the maximum steering angle with increasing image depth. The number of look directions is also preferably decreased when the number of lines or line density of the image is increased; when the number of transmit focal zones is increased; when the amount of deadtime per PRI is increased; when the number of transmissions per image line is increased (e.g., for synthetic aperture, pulse inversion harmonic imaging), when the number of simultaneous modes is increased (e.g., spectral Doppler together with 2D imaging), the size of the region of interest is increased (e.g., image zoom is decreased or turned off), the clinical application (e.g., changing from abdominal or peripheral vascular imaging to cardiac imaging), or changing from target to survey mode. When the number of simultaneously acquired lines is increased by increasing multiline acquisition, the number of look directions can be increased.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A harmonic ultrasonic spatially compounded diagnostic imaging system, comprising:
    a transducer array;
    a transmitter coupled to the transducer array, the transmitter applying transmit signals to the transducer array at a fundamental frequency, the transmit signals causing the transducer array to direct ultrasonic signals toward a target from a plurality of different look directions;
    a receive beamformer coupled to the transducer array, the beamformer generating echo signals from the target at each of the plurality of different look directions responsive to the ultrasonic signals being directed toward the look direction;
    a filter receiving the echo signals and passing echo signals having a frequency that are a harmonic of the fundamental frequency; and
    a compound image processor coupled to the filter to receive the echo signals passed by the filter, the image processor spatially compounding the received echo signals from each of the different look directions to form a spatially compounded image.

2. The ultrasonic diagnostic imaging system of claim 1, wherein the transmit signals comprise signals having a band of frequencies that includes the fundamental frequency.

3. The ultrasonic diagnostic imaging system of claim 1, wherein the transmit signals comprise signals substantially exhibiting a single fundamental frequency.

4. The ultrasonic diagnostic imaging system of claim 1, wherein the maximum angle of the different look directions is varied in response to a change in image depth.

5. The ultrasonic diagnostic imaging system of claim 1, wherein the compound image processor forms spatially compounded images in real time while the transducer array is operated to acquire target echoes at a plurality of look directions.

6. The ultrasonic diagnostic imaging system of claim 1, wherein the spatially compounded image comprises a three dimensional image.

7. The ultrasonic diagnostic imaging system of claim 1, wherein the spatially compounded image comprises a spatially compounded Doppler processed image indicative of moving ultrasound scatterers in the target.

8. The ultrasonic diagnostic imaging system of claim 7, wherein the spatially compounded Doppler processed image comprises a three dimensional spatially compounded image.

9. The ultrasonic diagnostic imaging system of claim 1, wherein the spatially compounded image comprises a real time spatially compounded image.

10. The ultrasonic diagnostic imaging system of claim 1, wherein the harmonic comprises a second harmonic of the fundamental frequency.

11. The ultrasonic diagnostic imaging system of claim 1, wherein the harmonic echo signals comprise tissue harmonic echo signals.

12. The ultrasonic diagnostic imaging system of claim 1, wherein the filter comprises a pulse inversion processor.

13. A harmonic ultrasonic spatially compounded diagnostic imaging system, comprising:
    a transducer array;
    a transmitter coupled to the transducer array, the transmitter applying transmit signals to the transducer array at a fundamental frequency, the transmit signals causing the transducer array to direct a main lobe of ultrasonic signals at the fundamental frequency toward a target from a first set of different look directions and to direct a grating lobe of the ultrasonic signals at the fundamental frequency in a second set of directions corresponding to respective look directions in the first set, each of the directions in the second set being different from the respective look directions in the first set;

a receive beamformer coupled to the transducer array, the beamformer generating echo signals from the target through a main lobe of ultrasonic signals at a harmonic of the fundamental frequency at each of the plurality of different look directions responsive to the ultrasonic signals at the fundamental frequency in the main lobe being directed toward each look direction, the receive beamformer further generating echo signals through a grating lobe of ultrasonic signals at the harmonic of the fundamental frequency from a third set of directions corresponding to respective look directions in the first set, each of the directions in the third set being different from respective directions in the second set and from respective look directions in the first set;

a filter receiving the echo signals and passing echo signals having a frequency that are a harmonic of the fundamental frequency; and a compound image processor coupled to the filter to receive the echo signals passed by the filter, the image processor compounding the received echo signals from each of the different look directions to form a spatially compounded image.

14. The ultrasonic diagnostic imaging system of claim 13, wherein the transmit signals comprise signals having a band of frequencies that includes the fundamental frequency.

15. The ultrasonic diagnostic imaging system of claim 13, wherein the transmit signals comprise signals exhibiting substantially a single fundamental frequency.

16. The ultrasonic diagnostic imaging system of claim 13, wherein the maximum angle of the different look directions is varied in response to a change in image depth.

17. The ultrasonic diagnostic imaging system of claim 13, wherein the compound image processor forms spatially compounded images in real time while the transducer array is operated to acquire target echoes at a plurality of look directions.

18. The ultrasonic diagnostic imaging system of claim 13, wherein the spatially compounded image comprises a three dimensional image.

19. The ultrasonic diagonostic imaging system of claim 13, wherein the spatially compounded image comprises a spatially compounded Doppler processed image indicative of moving ultrasound scatterers in the target.

20. The ultrasonic diagnostic imaging system of claim 19, wherein the spatially compounded Doppler processed image comprises a three dimensional spatially compounded image.

21. The ultrasonic diagnostic imaging system of claim 13, wherein an angle between the main lobe of ultrasonic signals at the fundamental frequency and the grating lobe of the ultrasonic signals at the fundamental frequency is substantially 90 degrees.

22. The ultrasonic diagnostic imaging system of claim 13, wherein the spatially compounded image comprises a real time spatially compounded image.

23. The ultrasonic diagnostic imaging system of claim 13, wherein the harmonic comprises a second harmonic of the fundamental frequency.

24. The ultrasonic diagnostic imaging system of claim 13, wherein the harmonic comprises a non-linear signal returned in response to the transmission of a linear fundamental frequency signal.

25. The ultrasonic diagnostic imaging system of claim 13, wherein the filter comprises a pulse inversion processor.

26. A harmonic ultrasonic spatially compounded diagnostic imaging system operable in response to the setting of a plurality of operating parameters, comprising:

an array transducer which is operated to acquire echoes from a target at a plurality of different look directions, the echoes being at a frequency that is a harmonic of a frequency of a signal that is transmitted by the array transducer; and a compound image processor responsive to changes of one or more operating parameters, the image processor compounding echo information of different look directions to form a spatially compounded image, the number of different look directions that are combined to form a compounded image being variable in response to changes of the one or more operating parameters.

27. The ultrasonic diagnostic imaging system of claim 26, wherein one of the operating parameters is image depth.

28. The ultrasonic diagnostic imaging system of claim 26, wherein one of the operating parameters is the number of lines in an image.

29. The ultrasonic diagnostic imaging system of claim 26, wherein one of the operating parameters is the density of lines in an image.

30. The ultrasonic diagnostic imaging system of claim 26, wherein one of the operating parameters is the number of transmit focal zones.

31. The ultrasonic diagnostic imaging system of claim 26, wherein one of the operating parameters is the amount of deadtime per pulse repetition interval.

32. The ultrasonic diagnostic imaging system of claim 26, wherein one of the operating parameters is the number of lines acquired per transmission.

33. The ultrasonic diagnostic imaging system of claim 26, wherein one of the operating parameters is the number of transmissions per image line.

34. The ultrasonic diagnostic imaging system of claim 33, wherein the array transducer transmits multiple times per image line during at least one of synthetic aperture operation and pulse inversion harmonic imaging operation.

35. The ultrasonic diagnostic imaging system of claim 33, wherein the array transducer produces multiple image lines in response to one pulse transmission.

36. The ultrasonic diagnostic imaging system of claim 26, wherein one of the operating parameters is the number of simultaneous imaging modes.

37. The ultrasonic diagnostic imaging system of claim 26, wherein one of the operating parameters is the size of an image region of interest.

38. The ultrasonic diagnostic imaging system of claim 37, wherein the size of a region of interest changes in response to changes in image zoom.

39. The ultrasonic diagnostic imaging system of claim 26, wherein one of the operating parameters is clinical application.

40. The ultrasonic diagnostic imaging system of claim 26, wherein one of the operating parameters is the selection of survey or target mode of operation.

41. The ultrasonic diagnostic imaging system of claim 26, wherein the maximum steering angle of the different look directions is varied in response to a change in image depth.

42. The ultrasonic diagnostic imaging system of claim 26, wherein the array transducer is operated to acquire images at one of a plurality of different acquisition frame rates, and wherein the number of echo signals from different look directions that are combined to form a compounded image by the compound image processor is related to the acquisition frame rate at which the array transducer is operated.

43. The ultrasonic diagnostic imaging system of claim 26, wherein the compound image processor forms spatially compounded images for real time display while the array transducer is operated to acquire target echoes at a plurality of look directions.

44. The ultrasonic diagnostic imaging system of claim 26, wherein the harmonic comprises a second harmonic of the fundamental frequency.

45. A method of forming a harmonic ultrasonic spatially compounded image, comprising:
   transmitting ultrasonic signals at a fundamental frequency having a main lobe and a grating lobe, the main lobe being directed at a target in a set of look directions while the grating lobe is directed in a respective set of second directions, each of the second directions being different from the respective look direction;
   receiving ultrasonic signals at a harmonic frequency having a main lobe and a grating lobe, the main lobe being directed at a target in each of the look directions while the ultrasonic signals at the fundamental frequency are being directed in the look direction, the grating lobe of the harmonic frequency being directed in a set of third directions, each of the third directions being different from the corresponding second direction for each of the respective look directions; and
   generating a spatially compounded image from the received ultrasonic signals at the harmonic frequency.

46. The method of claim 45 wherein the act of transmitting ultrasonic signals at a fundamental frequency comprises transmitting ultrasonic signals at substantially a single frequency.

47. The method of claim 45 wherein the act of transmitting ultrasonic signals at a fundamental frequency comprises transmitting ultrasonic signals at a range of frequencies.

48. The method of claim 45 wherein the act of transmitting ultrasonic signals at a fundamental frequency having a main lobe and a grating lobe comprises transmitting ultrasonic signals at a fundamental frequency having a main lobe that is at an angle of substantially 90 degrees from the grating lobe.

49. The method of claim 45 wherein the maximum angle of the different look directions is varied in response to a change in image depth.

50. The method of claim 45, wherein the act of generating a spatially compounded image from the received ultrasonic signals at the harmonic frequency comprises generating a spatially compounded image in real time.

51. The method of claim 45, wherein the act of generating a spatially compounded image from the received ultrasonic signals at the harmonic frequency comprises generating a three dimensional spatially compounded image.

52. The method of claim 45, wherein the act of generating a spatially compounded image from the received ultrasonic signals at the harmonic frequency comprises generating a spatially compounded Doppler processed image indicative of moving ultrasound scatterers in the target.

53. The method of claim 52, wherein the act of generating a spatially compounded Doppler processed image indicative of moving ultrasound scatterers in the target comprises generating a three dimensional spatially compounded Doppler processed image indicative of moving ultrasound scatterers in the target.

54. The method of claim 45 wherein the act of receiving ultrasonic signals at the harmonic frequency comprises receiving ultrasonic signals at a second harmonic of the fundamental frequency.

55. The method of claim 45, further comprising separating received ultrasonic signals at the harmonic frequency from received ultrasonic signals at the fundamental frequency.

56. The method of claim 55, wherein the act of separating comprises filtering.

57. The method of claim 55, wherein the act of separating comprises pulse inversion processing.

58. A method of forming a harmonic ultrasonic spatially compounded image, comprising:
   transmitting ultrasonic signals at a fundamental frequency having a main lobe directed at a target in a set of look directions;
   receiving ultrasonic signals at a harmonic frequency having a main lobe directed at a target in each of the look directions while the ultrasonic signals at the fundamental frequency are being directed in the look direction; and
   generating a spatially compounded image from the received ultrasonic signals at the harmonic frequency.

59. The method of claim 58 wherein the act of transmitting ultrasonic signals at a fundamental frequency comprises transmitting ultrasonic signals at substantially a single frequency.

60. The method of claim 58 wherein the act of transmitting ultrasonic signals at a fundamental frequency comprises transmitting ultrasonic signals at a range of frequencies.

61. The method of claim 58 wherein the maximum angle of the different look directions is varied in response to a change in image depth.

62. The method of claim 58, wherein the act of generating a spatially compounded image from the received ultrasonic signals at the harmonic frequency comprises generating a spatially compounded image in real time.

63. The method of claim 58, wherein the act of generating a spatially compounded image from the received ultrasonic signals at the harmonic frequency comprises generating a three dimensional spatially compounded image.

64. The method of claim 58, wherein the act of generating a spatially compounded image from the received ultrasonic signals at the harmonic frequency comprises generating a spatially compounded Doppler processed image indicative of moving ultrasound scatterers in the target.

65. The method of claim 64, wherein the act of generating a spatially compounded Doppler processed image indicative of moving ultrasound scatters in the target comprises generating a three dimensional spatially compounded Doppler processed image indicative of moving ultrasound scatterers in the target.

66. The method of claim 58, wherein the act of receiving ultrasonic signals at a harmonic frequency comprises receiving ultrasonic signals at a second harmonic of the fundamental frequency.

67. The method of claim 58, further comprising separating received ultrasonic signals at the harmonic frequency from received ultrasonic signals at the fundamental frequency.

68. The method of claim 67, wherein the act of separating comprises filtering.

69. The method of claim 67, wherein the act of separating comprises pulse inversion processing.

70. A method of forming a harmonic ultrasonic spatially compounded image with an ultrasonic imaging system having a plurality of different variable operating parameters, comprising:

acquiring a plurality of ultrasonic echoes from a target from a plurality of different look directions by transmitting ultrasound signals having a fundamental frequency and receiving ultrasound signals having a frequency that is a harmonic of the fundamental frequency; and spatially compounding a plurality of the ultrasonic echoes chosen in relation to the setting of an operating parameter.

71. The method of claim 70, wherein one of the operating parameters is image depth.

72. The method of claim 70, wherein the maximum steering angle of the different look directions is varied in response to a change in image depth.

73. The method of claim 70, wherein one of the operating parameters is the number of lines in an image.

74. The method of claim 70, wherein one of the operating parameters is the density of lines in an image.

75. The method of claim 70, wherein one of the operating parameters is the number of transmit focal zones.

76. The method of claim 70, wherein one of the operating parameters is the amount of deadtime per pulse repetition interval.

77. The method of claim 70, wherein one of the operating parameters is the number of lines acquired per transmission.

78. The method of claim 70, wherein one of the operating parameters is the number of transmissions per image line.

79. The method of claim 70, wherein one of the operating parameters is the number of simultaneous imaging modes.

80. The method of claim 70, wherein one of the operating parameters is the size of an image region of interest.

81. The method of claim 70, wherein one of the operating parameters is clinical application.

82. The method of claim 70, wherein one of the operating parameters is the selection of survey or target mode of operation.

83. A method of forming a harmonic ultrasonic spatially compounded image comprising:

acquiring a plurality of ultrasonic images of a region of the body from different look directions by directing ultrasound signals at a fundamental frequency into the body and receiving ultrasound signals from the body at a frequency that is a harmonic of the fundamental frequency; and compounding a number of the ultrasonic images chosen in relation to an acceptable display frame rate of the spatially compounded ultrasonic images.

84. A method of forming a harmonic ultrasonic spatially compounded image, comprising:

acquiring a plurality of ultrasonic images of a region of the body which exhibit different look directions by means of an array transducer transmitting ultrasound signals into the body at a fundamental frequency and receiving ultrasound signals from the body at a frequency that is a harmonic of the fundamental frequency;

compounding a number of the ultrasonic images to form a spatially compounded ultrasonic image; and displaying the spatially compounded ultrasonic image at a display frame rate, wherein the number of images which are compounded to form the spatially compounded image is varied in response to the setting of one or more of the parameters of: image display depth, frame acquisition rate, number of scanlines, image line density, number of transmit focal zones, amount of deadtime per PRI, number of transmissions per image line, depth of region of greatest compounding, clinical application, number of simultaneous modes, size of region of interest, and mode of operation.

* * * * *

UNITED STATES PATENT AND TRADEMARK OFFICE
CERTIFICATE OF CORRECTION

PATENT NO.      : 6,544,177 B1
DATED           : April 8, 2003
INVENTOR(S)     : Robinson It is certified that error appears in the above-identified patent and that said Letters Patent is hereby corrected as shown below:

<u>Title page,</u>
Item [*] Notice, should read -- Subject to any disclaimer, the term of this patent is extended or adjusted under 35 U.S.C. 154(b) by 61 days. --

Signed and Sealed this

Twenty-fourth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,544,177 B1
DATED : April 8, 2003
INVENTOR(S) : Andrew L. Robinson, Robert R. Entrekin and James R. Jago It is certified that error appears in the above-identified patent and that said Letters Patent is hereby corrected as shown below:

Title page,
Item [75], Inventors, "Andrew L. Robinson, Bellevue, WA (US)" should read
-- Andrew L. Robinson, Bellevue, WA (US); Robert R. Entrekin, Kirkland, WA (US); James R. Jago, Seattle, WA (US) --

Column 2,
Line 53, "and $\lambda 0$ is the" should read -- and $\lambda$ is the --

Column 3,
Line 12, "these angles $\phi_3$, it is necessary" should read -- these angles $\phi$, it is necessary" --

Column 6,
Line 1, "transmit energies" should read -- and transmit energies --

Column 7,
Line 62, "the number component" should read -- the number of component --

Column 8,
Line 44, "extends he full 4.0" should read -- extends the full 4.0 --
Line 55, "illustrations that that at" should read -- illustrations that at --

Column 9,
Line 22, "declines the number of" should read -- declines, the number of --

Signed and Sealed this

Ninth Day of November, 2004

JON W. DUDAS
*Director of the United States Patent and Trademark Office*